United States Patent
Feurstein et al.

Patent Number: 6,022,136
Date of Patent: Feb. 8, 2000

[54] MIXING DEVICE

[75] Inventors: Markus Feurstein, Feldkirch-Tosters, Austria; Bruno Senn, Buchs; Jürgen Mertins, Gams, both of Switzerland

[73] Assignee: Ivoclar AG, Schaan, Liechtenstein

[21] Appl. No.: 09/056,314

[22] Filed: Apr. 7, 1998

Related U.S. Application Data

[60] Provisional application No. 60/054,898, Aug. 5, 1997.

[30] Foreign Application Priority Data

Apr. 11, 1997 [DE] Germany ............................ 197 15 118

[51] Int. Cl.[7] ...................................................... B01F 11/04
[52] U.S. Cl. ............................................. 366/209; 366/602
[58] Field of Search ..................................... 366/209, 210, 366/211, 213, 214, 215, 216, 217, 218, 239, 237, 110, 602; 269/55, 90, 93, 94, 135, 188, 216, 217, 234, 254 DF

[56] References Cited

U.S. PATENT DOCUMENTS

| | | |
|---|---|---|
| 1,489,024 | 4/1924 | Burnett ................................... 366/209 |
| 3,749,371 | 7/1973 | Folkenroth et al. . |
| 4,074,900 | 2/1978 | Drury ...................................... 366/210 |
| 4,890,931 | 1/1990 | Herold ................................... 366/216 |
| 5,184,893 | 2/1993 | Steele et al. ........................... 366/209 |
| 5,338,114 | 8/1994 | Steele ..................................... 366/216 |

FOREIGN PATENT DOCUMENTS

| | | |
|---|---|---|
| 27 45 476 A1 | 5/1978 | Germany . |
| 41 06 388 A1 | 9/1992 | Germany . |

*Primary Examiner*—Tony G. Soohoo
*Attorney, Agent, or Firm*—Alan S. Korman; John C. Thompson

[57] ABSTRACT

A mixing device has a swing arm and securing arms, for receiving and securing a mixing capsule within the mixing device, connected to the swing arm. The securing arms include at least one moveable securing arm that is movably connected to the swing arm and at least one stationary securing arm that is fixedly connected to the swing arm such that the moveable securing arm is moveable relative to the stationary securing arm. An inertia mass acts via at least one of the securing arms onto a mixing capsule received in the securing arms.

14 Claims, 2 Drawing Sheets

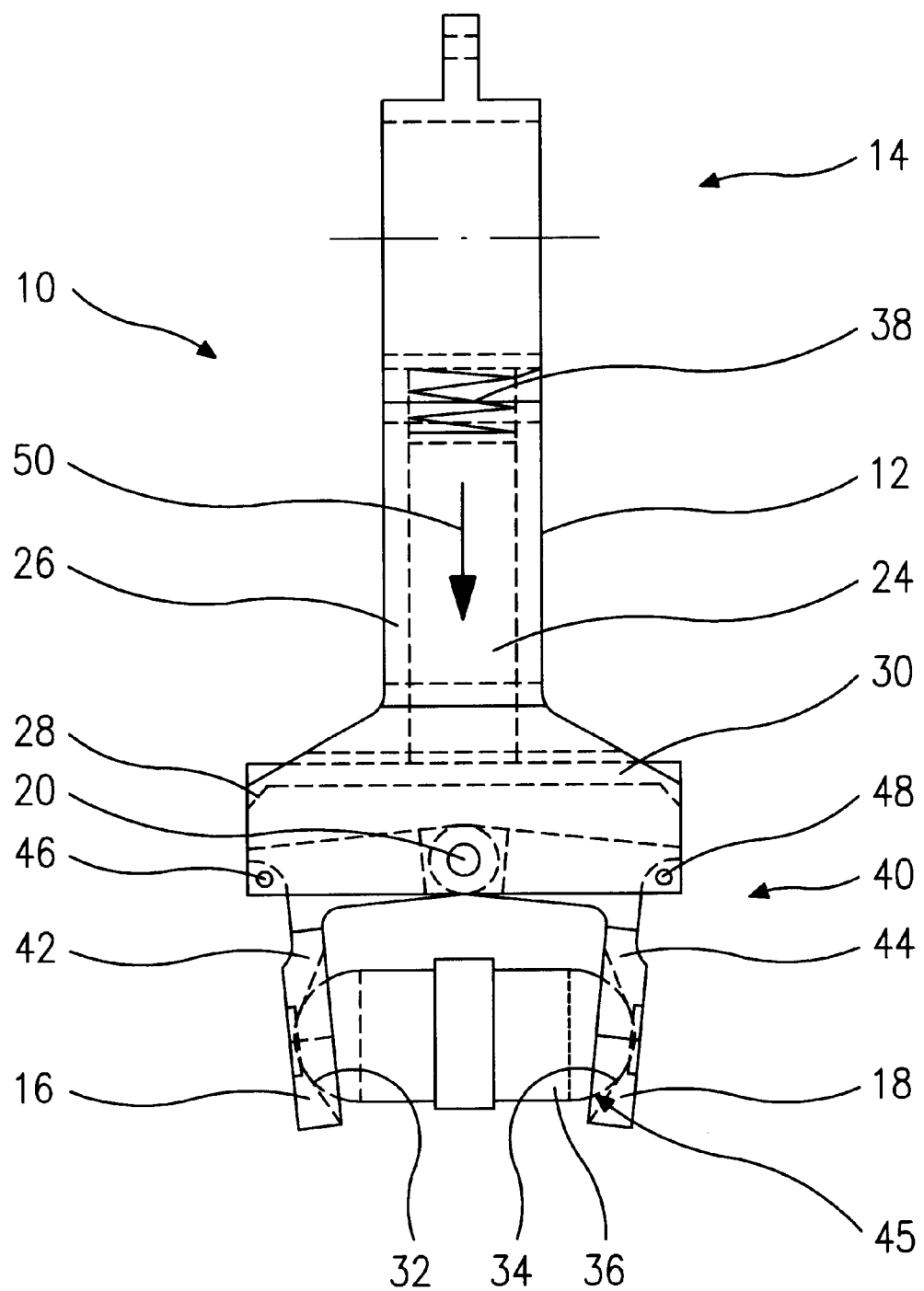
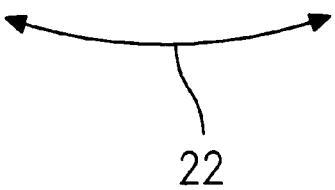

MIXING DEVICE

This is a continuation application of a U.S. Provisional Application 60/054,898 filed Aug. 5, 1999.

BACKGROUND OF THE INVENTION

The present invention relates to a mixing device comprising a swing arm for receiving a mixing capsule within securing arms whereby at least one securing arm is movably supported at the swing arm so that the two securing arms can be moved relative to one another.

Such a mixing device is, for example, known from U.S. Pat. No. 3,749,371. This document shows a mixing device with two spaced apart securing arms which support the mixing capsule that contains the dental material to be mixed.

Mixing capsules for dental materials are manufactured with different dimensions, and the respective mixing devices therefore require a spring-loaded support within the swing arm. Since the capsules are subjected to very high acceleration forces in order to ensure a sufficient mixing action of the amalgam, the prongs of the mixing device in the known device are thus subjected to high loads so that they must be embodied with sufficient stability in order to prevent breakage during operation. This requires that for the insertion of the capsules relatively great actuating forces must be expended.

Furthermore, mixing devices have been suggested in which the mixing capsules are received in a closed space and are thus securely contained. In this context, it has been suggested to introduce by movement of one of the securing arms a canting action in order to ensure a safe securing of the mixing capsule by canting. In this suggested solution it is especially disadvantageous that the canting can act only on one side so that during the return swing movement the canting force is greatly reduced, if not eliminated. The canting elements are thus subjected to great changing loads. The resulting corresponding wear can not ensure safe canting over an extended period of time.

A further example of such a mixing device is known from U.S. Pat. No. 4,074,900 in which the mixing capsule is secured in a closed chamber and a locked by a fork in the mixing position. Even though this solution exhibits reduced wear, it has not found acceptance because it requires a very stable embodiment of the securing arm similar to the aforementioned solution.

Since the securing arm swings or pivots, it is therefore not only necessary to increase the drive forces in order to ensure the same mixing result. Also, a stronger swinging load of the drive device results so that correspondingly strong oscillations, undesirable in dental practices, are introduced into the support of the mixing device.

Accordingly, in general, the comparatively light-weight spring-loaded mixing devices or forks have found greater acceptance whereby preferably hard and at the same time light-weight spring steel has been used for the mixing forks. A lateral introduction of the capsule is generally preferred. An example for such a solution is known from German Patent 41 06 388.

It is therefore an object of the present invention to provide a mixing device of the aforementioned kind which, in comparison to the prior art mixing devices, introduces a reduced amount of oscillations into the support for the mixing device but still ensures easy operation with secure hold of mixing capsules of different sizes.

SUMMARY OF THE INVENTION

A mixing device according to the present invention includes:

a swing arm;

securing arms, for receiving and securing a mixing capsule within the mixing device, connected to the swing arm;

the securing arms including at least one moveable securing arm that is movably connected to the swing arm and including at least one stationary securing arm that is fixedly connected to the swing arm such that the moveable securing arm is moveable relative to the stationary securing arm;

an inertia mass acting via at least one of the securing arms onto a mixing capsule received in the securing arms.

Advantageously, the swing arm is a mixing fork comprising two prongs forming the securing arms, wherein one of the prongs is pivotally supported to form the moveable securing arm, and wherein the inertia mass acts onto the moveable securing arm.

Advantageously, the mixing device further comprises abutments, wherein the two prongs are elbow levers, wherein the inertia mass acts on the two prongs, and wherein the abutments limit a movement stroke of the elbow levers.

The securing arms are one-armed levers and a centrifugal force generated by the inertia mass acts onto the mixing capsule in a 1:2 reducing ratio.

The mixing device further comprises a pressure spring positioned in the swing arm, wherein the swing arm has a pivot bearing and wherein the pressure spring is positioned between the inertia mass and the pivot bearing.

Advantageously, the securing arms have cup-shaped securing areas facing one another and the cup-shaped securing areas receive end faces of the mixing capsule.

The mixing device further comprises abutments for limiting a movement stroke of the securing arms, wherein, for receiving the mixing capsule, the securing arms are moved away from one another against the abutments so as to have a spacing there-between that allows snapping the mixing capsule into the securing areas with a brief spreading of the securing arms without having to move the securing arms farther apart.

A securing force of the securing arms is selected such that a sum of forces generated by the inertia mass and the pressure spring is substantially greater than the centrifugal force of the heaviest mixing capsule to be used with the mixing device.

Advantageously, one of the securing arms is a hook that compensates the centrifugal force of the mixing capsule and another one of the securing arms is a clamping element for the mixing capsule acting radially outwardly, wherein the inertia mass is positioned in the clamping element.

The mixing device may further comprise a pressure spring for pressing one of the securing arms against the mixing capsule.

The securing arms are preferably connected to a common pivot axis.

Advantageously, one of the securing arms is fixedly connected to the swing arm, is hook-shaped, and laterally supports the mixing capsule, the one securing arm having a U-shaped depression for receiving the mixing capsule.

The one securing arm supports end faces of the mixing capsule.

Surprisingly, the inventive mixing device provides the possibility to ensure with comparatively minimal weight a positive locking support of the mixing capsule. The inertia mass, which is forced outwardly by the centrifugal force, results in a dynamic increase of the securing force so that the securing force present at rest can be selected to be rather small. This simplifies removal from and loading of the mixing device. The inventive mixing device allows a precise guiding of the securing arms which is not cancelled even when the pivot movement (swing action) is combined with a wobble movement. The securing force is greatest when the greatest centrifugal force acts on the mixing capsule.

The inventive solution preferably suggests abutments which limit the movement of the securing arms. The spacing between the securing areas, respectively, the receiving opening is then somewhat smaller than the smallest capsule to be inserted so that the abutments cannot impede the action of the inertia mass and of the spring in any of the operating states but facilitates the introduction of the mixing capsule.

Preferably, a pressure spring is positioned between the inertia mass and the securing arm. It enhances in a simple manner the action of the inertia mass in the rest position of the mixing device. Preferably, the pressure spring is guided in a tubular securing section of the securing arm and has a spring action acting in the direction of the securing arm. In this design the last windings of the pressure spring enhance the action of the inertia mass so that the size of the inertia mass can be further reduced. Furthermore, the tubular design of the securing section provides for a comparatively simplified construction whereby it is understood that preferably high quality materials are used for the mixing device.

BRIEF DESCRIPTION OF THE DRAWINGS

The object and advantages of the present invention will appear more clearly from the following specification in conjunction with the accompanying drawings, in which:

FIG. 1 is a schematic view of a mixing device in a first embodiment of the invention;

DESCRIPTION OF PREFERRED EMBODIMENTS

Figure 2:
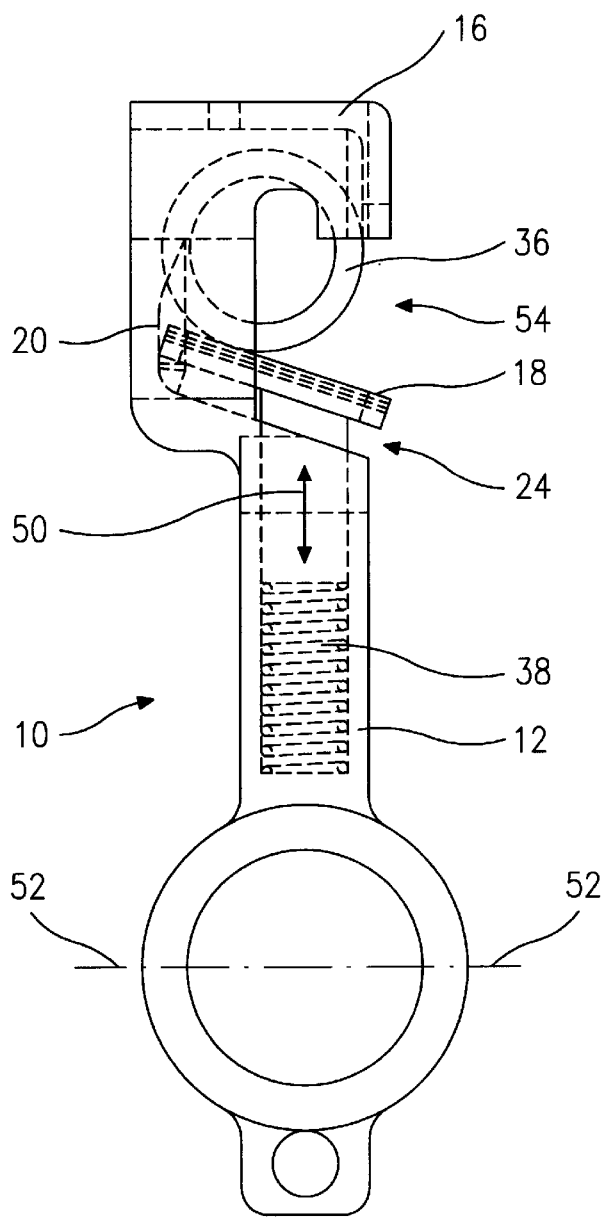
FIG. 2 is a schematic view of the inventive mixing device in a second embodiment of the invention.

The present invention will now be described in detail with the aid of several specific embodiments utilizing FIGS. 1–3.

The mixing device 10 represented in FIG. 1 comprises in a first embodiment a swing arm 12 which is supported in a manner known per se by a pivot bearing 14, as, for example, shown in German Patent 41 06 388, and further comprises two securing arms 16 and 18 connected to a pivot joint 20. The pivot or swing action is carried out in the direction of arrows 22 so that in this embodiment the axis of the pivot joint 20 extends substantially parallel to the axis of the swing arm 12.

According to a modified embodiment, it is suggested that the pivot axis extends at an angle of 90° relative to the non-represented swing axis, i.e., it extend substantially parallel to the plane of the drawing.

The swing arm 12 comprises an inertia mass 24 which is slidably supported in a tubular securing section 26 of the swing arm 12. The inertia mass 24 comprises in the represented embodiment two sockets 28 and 30 that extend laterally outwardly and act onto the securing arms 16 and 18. The securing arms 16 and 18 are in the form of bell cranks or elbow joints, both supported at the pivot joint 20. In the manner of a one-armed lever the action of the inertia mass 24 acts onto the securing arms 16 and 18 so that they move with their cup-shaped securing areas 32, 34 toward one another. Accordingly, a mixing capsule 36 received therebetween is clamped by the action of the inertia mass 24, enhanced by the action of the spring 38.

The securing arms 16 and 18, in the manner of a mixing fork 40, have prongs 42 and 44 which form the securing areas 32 and 34.

Preferably, the mixing capsule 36 is secured with its end faces in the securing areas 32 and 34 whereby, depending on the position of the securing arms, greater or smaller mixing capsules can be received. According to an alternative embodiment, it is suggested that the securing arms 16 and 18 laterally support the mixing capsule.

When the mixing device 10 is at rest, the prongs 42 and 44 can be spread counter to the action of the pressure springs 38 in order to insert or remove the mixing capsule 36 with the aid of its slanted surfaces 45. The prongs 42 and 44 cannot come into contact with one another because the action of the spring 38 is limited by the abutments 46 and 48 which are connected to the swing arm 12 and prevent that the pressure spring 38 acting on the inertia mass 24 forces the elbow levers 16 and 18 toward one another.

During mixing, a pivoting or swinging of the swing arm 12 in the direction of arrow 22 takes place. This movement generates a centrifugal force for the inertia mass 24 in the direction of arrow 50. Due to this centrifugal force, the securing arms 16 and 18 are forced toward one another during mixing so that the mixing capsule 36, which is also subjected to the centrifugal force, is secured to an even greater extent in comparison to the securing action by the spring 38 alone. The sum of the forces of the inertia mass 24 and of the spring 38 is such that even the heaviest mixing capsule 36 to be used with the inventive mixing device can not spread apart the securing arms 16 and 18.

A modified embodiment of the inventive mixing device can be seen in FIG. 2. Same parts are identified with identical reference numerals as in FIG. 1. In this embodiment, which is shown rotated by 90° relative to FIG. 1, the pivot action of the swing arm 12 takes place about the pivot axis 52. The pressure spring 38 is substantially longer than in the embodiment according to FIG. 1. Accordingly, the windings of the spring remote from the pivot axis 52 enhance the action of the inertia mass. In this embodiment, the two securing arms 16 and 18 are asymmetrical to one another, whereby the securing arm 16 engages about the mixing capsule 36 which is received in the U-shaped depression 54 of the securing arm 16 while the securing arm 18 presses onto the mixing capsule 36 from the opposite side. The securing arm 18 thus comprises the inertia mass 24, and the pressure spring 38 acts onto the arm 18 which is also partially used as an inertia mass.

Figure 3:
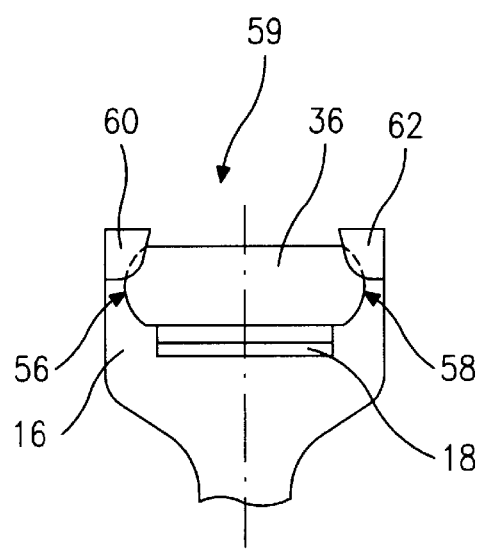
FIG. 3 is a plan view of the mixing device in the embodiment according to FIG. 2.

As can be seen in more detail in FIG. 3, the securing arm 16 secures the mixing capsule 36 at its end faces 56 and 58. This design allows the use of a comparatively minimal weight for the inventive swing arm 12, especially since the central area 59 of the mixing capsule 36 is not supported as in the embodiment according to FIG. 1 and is not covered by a portion of the swing arm 12.

The securing arm 18 in the embodiment according to FIGS. 2 and 3 is a plate supported by a pivot joint 20. The U-shaped depression 54 is limited at one side by the plate that is positioned at a slant relative to the depression 54. Due to this embodiment, the insertion of the mixing capsule 36 is facilitated so that even a one-hand operation of the inventive mixing device is possible. Preferably, the securing arm 18 is limited by a non-represented abutment in its movement in the direction of arrow 50 so that the two securing arms 16 and 18 in this embodiment can also not be moved too far apart.

According to a modified embodiment, an additional inertia mass 24 is provided between the pressure spring 38 and the securing arm 18. It further increases the securing force for the mixing capsule 36. Due to the one-sided support by the corner areas 60 and 62 of the securing arm 16 positioned opposite the securing arm 18, the required securing force is comparatively minimal so that it is preferred to use the securing arm 18 only as an inertia mass 24.

The pivot joint 20 in the embodiment according to FIGS. 2 and 3 can be embodied in any desired manner. For example, it is possible to provide thereat abutments of the securing arm 16 and thus of the swing arm 12 which have a pivot joint character for the securing arm 18. In this embodiment, it is ensured by correspondingly laterally arranged abutments that the plate-shaped securing arm 18 can not deflect laterally.

The present invention is, of course, in no way restricted to the specific disclosure of the specifications, and drawings, but also encompasses any modifications within the scope of the appended claims.

What is claimed is:

1. A mixing device comprising:
a swing arm having a pivot point at one end;
a pair of securing arms connected to the other end of said swing arm for receiving and securing a mixing capsule within said mixing device, said securing arms including at least one moveable securing arm that is moveably connected to said swing arm and including at least one stationary securing arm that is fixedly connected to said swing arm such that said moveable securing arm is moveable relative to said stationary securing arm; and
an inertia mass carried by the swing arm between the pivot point and the moveable securing arm and bearing against the one moveable securing arm when the swing arm is swinging to force the moveable securing arm to its closed capsule securing position.

2. A mixing device according to claim 1, wherein one of said securing arms is a hook that compensates the centrifugal force of the mixing capsule and wherein another one of said securing arms is a clamping element for the mixing capsule acting radially outwardly, wherein said inertia mass is positioned in said clamping element.

3. A mixing device according to claim 2, further comprising a pressure spring for pressing one of said securing arms against the mixing capsule.

4. A mixing device according to claim 2, wherein one of said securing arms is fixedly connected to said swing arm, is hook-shaped, and laterally supports the mixing capsule, said one securing arm having a U-shaped depression for receiving the mixing capsule.

5. A mixing device according to claim 4, wherein said one securing arm supports end faces of the mixing capsule.

6. A mixing device comprising:
a swing arm having a pivot point at one end;
a pair of securing arms for receiving and securing a mixing capsule within said mixing device, the securing arms being connected to the other end of the swing arm for movement between an open capsule receiving position and a closed capsule securing position, the securing arms including at least one moveable securing arm that is moveably secured to said swing arm; and
an inertia mass carried by the swing arm between the pivot point and the moveable securing arms and acting via at least one of said securing arms on a mixing capsule received in said securing arms.

7. A mixing device according to claim 6, wherein said swing arm is a mixing fork, wherein said securing arms are prongs, wherein one of said prongs is pivotally supported to form one of said moveable securing arms, and wherein said inertia mass acts on said one moveable securing arm.

8. A mixing device according to claim 7, wherein abutments are carried by the other end of the swing arms, wherein the two prongs are elbow levers, wherein said mass acts on said two prongs, and wherein said abutments limit movement stroke of said elbows.

9. A mixing device according to claim 6, further comprising a pressure spring positioned in said swing arm, wherein said swing arm has a pivot bearing, and wherein said pressure spring is positioned between said inertia mass and said pivot bearing and acts to move the swing arm to the closed capsule securing position.

10. A mixing device according to claim 9, wherein said securing arms have cup-shaped securing areas facing one another and wherein said cup-shaped securing areas receive end faces of the mixing capsule.

11. A mixing device according to claim 10, further comprising abutments for limiting a movement stroke of said securing arms, wherein, for receiving the mixing capsule, said securing arms are moved away from one another against said abutments so as to have a spacing therebetween that allows snapping the mixing capsule into said securing areas with a brief spreading of said securing arms without having to move said securing arms farther apart.

12. A mixing device according to claim 6, wherein said securing arms are connected to a common pivot axis.

13. A mixing device according to claim 6 wherein each of said securing arms is in the form of a bell crank, adjacent legs of the bell cranks being pivotally connected to the swing arm.

14. A mixing device comprising:
a swing arm having a pivot point at one end;
a pair of moveable securing arms connected to the other end of the swing arm for receiving and securing a mixing capsule within the mixing device, each of said moveable securing arms being pivotally connected to the swing arm for movement between an open capsule receiving position and a closed capsule securing position; and
an inertia mass carried by the swing arm between the pivot point and the moveable securing arms and capable of bearing upon the moveable securing arms when the swing arm is swinging to force the moveable securing arms to their closed capsule securing position.

* * * * *